United States Patent
Koren et al.

(10) Patent No.: US 9,147,102 B2
(45) Date of Patent: Sep. 29, 2015

(54) METHOD AND SYSTEM FOR MEASURING BUMPS BASED ON PHASE AND AMPLITUDE INFORMATION

(75) Inventors: Shimon Koren, Haifa (IL); Or Shur, Haifa (IL); Yacov Malinovich, Kiryat Tivon (IL); Gilad Golan, Raanana (IL)

(73) Assignee: CAMTEK LTD., Migdal Haemek (IL)

( * ) Notice: Subject to any disclaimer, the term of this patent is extended or adjusted under 35 U.S.C. 154(b) by 368 days.

(21) Appl. No.: 13/342,119

(22) Filed: Jan. 2, 2012
(Under 37 CFR 1.47)

(65) Prior Publication Data
US 2013/0170712 A1 Jul. 4, 2013

(51) Int. Cl.
G06K 9/32 (2006.01)
G06K 9/00 (2006.01)
G02B 21/00 (2006.01)
G01N 21/956 (2006.01)
G01B 11/06 (2006.01)

(52) U.S. Cl.
CPC ...... G06K 9/00127 (2013.01); G01N 21/95607 (2013.01); G01N 21/95684 (2013.01); G02B 21/0016 (2013.01); G01B 11/0608 (2013.01); G02B 21/0056 (2013.01)

(58) Field of Classification Search
CPC ........... G06K 9/00127; G01B 11/0608; G01N 21/95607; G02B 21/0016; G02B 2/0056
See application file for complete search history.

(56) References Cited

U.S. PATENT DOCUMENTS

| | | | | |
|---|---|---|---|---|
| 5,555,474 A | * | 9/1996 | Ledger | 356/632 |
| 5,621,811 A | * | 4/1997 | Roder et al. | 382/147 |
| 6,016,202 A | * | 1/2000 | Fuchs et al. | 356/432 |
| 6,118,533 A | * | 9/2000 | Banet et al. | 356/450 |
| 6,177,682 B1 | * | 1/2001 | Bartulovic et al. | 250/559.44 |
| 6,411,406 B1 | * | 6/2002 | Kreuzer | 359/10 |
| 6,650,790 B1 | * | 11/2003 | Arbeiter et al. | 382/275 |
| 6,671,019 B1 | * | 12/2003 | Petschek et al. | 349/129 |
| 6,672,739 B1 | * | 1/2004 | Argyle et al. | 362/259 |
| 7,194,112 B2 | * | 3/2007 | Chen et al. | 382/106 |
| 7,286,137 B2 | * | 10/2007 | Baba-Ali | 345/606 |
| 7,466,854 B2 | * | 12/2008 | Sawa et al. | 382/145 |
| 7,877,722 B2 | * | 1/2011 | Duffy et al. | 716/55 |
| 8,437,533 B2 | * | 5/2013 | Kim et al. | 382/141 |
| 2002/0051566 A1 | * | 5/2002 | Yamashita | 382/151 |
| 2002/0075462 A1 | * | 6/2002 | Kessler et al. | 355/22 |
| 2002/0154812 A1 | * | 10/2002 | Chen et al. | 382/154 |
| 2002/0172131 A1 | * | 11/2002 | Burr | 369/103 |
| 2002/0195538 A1 | * | 12/2002 | Dowsk et al. | 250/201.2 |
| 2003/0174880 A1 | * | 9/2003 | Sakamoto et al. | 382/154 |
| 2004/0146196 A1 | * | 7/2004 | Van Heel | 382/154 |
| 2005/0052705 A1 | * | 3/2005 | Hersch et al. | 358/3.28 |
| 2005/0185173 A1 | * | 8/2005 | Hau-Riege | 356/237.5 |
| 2005/0265595 A1 | * | 12/2005 | Sawa et al. | 382/149 |
| 2006/0002608 A1 | * | 1/2006 | Haddon et al. | 382/173 |
| 2006/0083420 A1 | * | 4/2006 | Kawaguchi | 382/149 |

(Continued)

OTHER PUBLICATIONS

Tellambura et al. "Phase Optimization Criterion for Reducing Peak-to-Average Power Ratio in OFDM" IEEE Electronic Letters Jan. 22, 1998, vol. 34, No. 2, pp. 1-2.*

*Primary Examiner* — Jayesh A Patel
*Assistant Examiner* — Mia M Thomas
(74) *Attorney, Agent, or Firm* — Reches Patents

(57) ABSTRACT

A method and device for measuring a height of a microscopic structure such as solder bumps. For simplicity of explanation, the invention is described with respect to phase information and amplitude information wherein phase detection and calculation algorithms are being used.

16 Claims, 8 Drawing Sheets

(56) References Cited

U.S. PATENT DOCUMENTS

| | | | |
|---|---|---|---|
| 2006/0269875 A1* | 11/2006 | Granik | 430/311 |
| 2007/0115432 A1* | 5/2007 | Thibos | 351/246 |
| 2007/0247630 A1* | 10/2007 | Herring | 356/458 |
| 2008/0008349 A1* | 1/2008 | Binnig et al. | 382/100 |
| 2008/0179503 A1* | 7/2008 | Camargo et al. | 250/216 |
| 2009/0027747 A1* | 1/2009 | Lee et al. | 359/15 |
| 2009/0257672 A1* | 10/2009 | Sullender | 382/260 |
| 2010/0021124 A1* | 1/2010 | Koos et al. | 385/141 |
| 2010/0022869 A1* | 1/2010 | Kimura | 600/419 |
| 2010/0060897 A1* | 3/2010 | Gustafsson | 356/458 |
| 2010/0092041 A1* | 4/2010 | Kim et al. | 382/106 |
| 2010/0260409 A1* | 10/2010 | Ben-Levy | 382/141 |
| 2011/0117478 A1* | 5/2011 | Kitamura | 430/2 |
| 2011/0141273 A1* | 6/2011 | Dubois | 348/135 |
| 2011/0218432 A1* | 9/2011 | Tumer | 600/431 |
| 2011/0255097 A1* | 10/2011 | Golan et al. | 356/496 |
| 2012/0075456 A1* | 3/2012 | Seitz | 348/79 |
| 2013/0128282 A1* | 5/2013 | Ishigaki | 356/610 |
| 2013/0335851 A1* | 12/2013 | Wilson et al. | 360/53 |

* cited by examiner

52

54

Phase image 82

Amplitude image 81

Mask 83

Elected phase pixels 84

80

METHOD AND SYSTEM FOR MEASURING BUMPS BASED ON PHASE AND AMPLITUDE INFORMATION

BACKGROUND OF THE INVENTION

Electrical circuits and other samples may include multiple microscopic structures such as bumps that should be measured for various purposes.

FIG. 1 illustrates a prior art portion 10 of a semiconductor chip with multiple solder bumps.

A bump has a shape that may be approximated by a dome. The manufacturing process of the bump mandates certain height to diameter ratios of the bump.

There are several known optical height metrology methods. The most sensitive methods are based on phase detection using various interferometric principles.

It is known in the art that the measurement of phase is a noisy process and that phase information is noisy. This noise can be more severe when measuring structures such as bumps due to their shape.

Digital holographic microscopes such as the DHM R1100™ of Lyncee Tec of Lausanne Switzerland use two laser sources that can be simultaneously or alternatively switched or continuously operate to illuminate a sample. Light from the sample and references beams are processed to provide phase information and amplitude information. The structure of the DHM R1100 is described in "Digital holographic reflectometry". Optics Express Vol. 18, No. 4, 15 Feb. 2010, which is incorporated herein by reference.

The mentioned above interferometric based optical height metrology method can measure a height maximum range that is limited by the wavelength of the light. The optical phenomena that limit the range called "phase warp".

There are numerous methods known for "phase un-warp" algorithm, all use various assumptions about phase continuity. Such methods are not applicable to bump metrology due to intrinsic phase discontinuity due to bump geometry.

The phase information exhibits phase ambiguity. FIGS. 2a and 2b illustrate phase height ambiguities for two different phase offsets.

Curve 22 of FIG. 2a and curve 24 of FIG. 2b represent the relationship between phase information (y-axis) and height (x-axis) of a microscopic structure represented by the phase information.

Phase information can be defined in a range of 2 pi (the phase can range between minus pi and plus pi), while "phase offset" (PO) defines the starting point of the phase extraction algorithm.

FIG. 2a illustrates the relationship between phase information and height obtained by an calculation based on and image created by interferometer that is set to have a phase offset of zero while FIG. 2b illustrates this relationship for a phase offset of minus pi.

The relationship can be defined similarly for any phase offset in a given range. Eventually, the linear slope of this relationship is specifically defined for any optical setup.

FIGS. 2a and 2b illustrate that there is intrinsic height uncertainty exists in this kind of behavior. A phase range that spans between minus pi and plus pi is mapped to height ranges each having a range size of Hr. In this case the same phase information value shall be measured for different heights located at the same position (offset from the beginning of the height range) at different height ranges.

In mathematical terms and assuming the Hm is the measured height then:

Phase($Hm$)=phase($Hm+N*Hr$).

More than that, FIGS. 2a and 2b show discontinuities—"phase warp"—a jump from —pi to +pi. When operating at there discontinuities the height measurement will suffer from possible errors as small noises can result in a very large offset in the height measurement. For example, for PO=0, the discontinuity is located around any modulo of ½ Hr—at any height that can be represented by Hr*(0.5+N), N being a positive integer.

There is a growing need to provide fast and accurate means for measuring the height of microscopic structures.

SUMMARY

A device may be provided for measuring a height of a microscopic structure, the device may include: a storage circuit arranged to store information that may include amplitude information and phase information, the information is indicative of a shape and a size of the microscopic structure; a mask generation circuit arranged to threshold pixels of the amplitude information to provide a mask that may include masked amplitude pixels; a phase information circuit arranged to apply the mask on the phase information to provide masked phase pixels; select, out of the masked phase pixels, selected phase pixels that correspond to a phase criterion, the selected phase pixels have selected phase pixels attribute values; find, out of the phase information, elected phase pixels that have the selected phase pixel attribute values; and a height calculation circuit arranged to generate a height measurement result based the elected phase pixels.

The mask generation circuit may be arranged to check whether the mask has at least a predetermined number of pixels; if the mask does not have the at least predetermined number of pixels then the mask generation circuit may be arranged to lower the amplitude information to provide a modified amplitude threshold; and the phase information circuit may be arranged to threshold the pixels of the amplitude information using the modified amplitude threshold.

The microscopic structure may be a solder bump.

The phase criterion may represent a statistical criterion selected out of an average, a standard deviation, a weight average or a median or any other statistical distribution criteria.

The height calculation circuit may be arranged to generate a height measurement result based on a predefined approximation of the shape of the microscopic structure and on the elected phase pixels.

A method can be provided for measuring a height of a microscopic structure, the method may include: receiving or generating information that may include amplitude information and phase information, the information is indicative of a shape and a size of the microscopic structure; thresholding pixels of the amplitude information to provide a mask that may include masked amplitude pixels; applying the mask on the phase information to provide masked phase pixels; selecting, out of the masked phase pixels, selected phase pixels that correspond to a phase criterion, the selected phase pixels have selected phase pixels attribute values; finding, out of the phase information, elected phase pixels that have the selected phase pixel attribute values; and generating a height measurement result based the elected phase pixels.

The method may include checking whether the mask has at least a predetermined number of pixels; if the mask does not have the at least predetermined number of pixels then lowering the amplitude information to provide a modified amplitude threshold; and thresholding the pixels of the amplitude information using the modified amplitude threshold.

The microscopic structure may be a solder bump.

The phase criterion, may represent a statistical criterion selected out of an average, a standard deviation, a weight average, a median.

The method may include generating a height measurement result by generating an approximation of the shape and size of the microscopic structure based on a predefined approximation of the shape of the microscopic structure and on the elected phase pixels.

A device may be provided for measuring a height of a microscopic structure, the device may include: a storage circuit for storing a phase image and an amplitude image of the microscopic structure; a reminder height calculation circuit arranged to calculate reminder height estimates based on the phase image pixels; a feature extractor arranged to detect an edge of the microscopic structure on a surface of an object; a size attribute circuit arranged to calculate a size attribute of the microscopic structure based on a size of a shape defined by the edge of the microscopic structure; a selection circuit arranged to select a selected height range out multiple height ranges based upon the size attribute of the microscopic structure and an allowable relationship between the size attribute and height values of the microscopic structure; and a height calculation circuit arranged to calculate an actual height of the microscopic structure based on the selected height range and the reminder height estimate.

The device may include a phase offset circuit that may be arranged to set a phase offset of an interferometer that may be arranged to obtain the phase image and the amplitude image in response to an expected height of the microscopic structure.

The microscopic structure may be a bump and the size attribute may be a diameter of the bump.

The height calculation circuit may be arranged to calculate actual height values form multiple phase image pixels of the phase image; and process the actual height values of the multiple phase image pixels to provide the actual height of the microscopic structure.

The phase offset circuit may be arranged to set a phase offset of the interferometer so that the expected bump height is mapped to a center of a continuous range of phase values.

The device may include a mask generation circuit arranged to threshold pixels of the amplitude image to provide a mask that may include masked amplitude pixels; and a phase information circuit arranged to apply the mask on the phase information to provide masked phase pixels; select, out of the masked phase pixels, selected phase pixels that correspond to a phase criterion, the selected phase pixels have selected phase pixels attribute values; find, out of the phase information, elected phase pixels that have the selected phase pixel attribute values; and the reminder height calculation circuit may be arranged to calculate reminder height estimates based on the elected phase pixels of the phase image pixels.

A method may be provided for measuring a height of a microscopic structure, the method may include: generating or receiving a phase image and an amplitude image of the microscopic structure; calculating reminder height estimates based on the phase image pixels; detecting the edge of the microscopic structure on a surface of an object; calculating size attribute of the microscopic structure based on a size of a shape defined by the edge of the microscopic structure; selecting a selected height range out multiple height ranges based upon the size attribute of the microscopic structure and an allowable relationship between the size attribute and height values of the microscopic structure; and calculating an actual height of the microscopic structure based on the selected height range and the reminder height estimate.

The method may include setting a phase offset of an interferometer that obtained the phase image and the amplitude image in response to an expected height of the microscopic structure.

The microscopic structure may be a bump and the size attribute may be a diameter of the bump.

The method may include calculating actual height values form multiple phase image pixels of the phase image; and processing the actual height values of the multiple phase image pixels to provide the actual height of the microscopic structure.

The generating of the phase image and the amplitude image may include setting a phase offset of an interferometer based on an expected height of the microscopic structure so that the expected bump height is mapped to a center of a continuous range of phase values.

The method may include thresholding pixels of the amplitude information to provide a mask that may include masked amplitude pixels; applying the mask on the phase information to provide masked phase pixels; selecting, out of the masked phase pixels, selected phase pixels that correspond to a phase criterion, the selected phase pixels have selected phase pixels attribute values; finding, out of the phase information, elected phase pixels that have the selected phase pixel attribute values; the calculating of the reminder height estimates is based on the elected phase pixels of the phase image pixels.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The following text will refer to bumps (especially solder bumps) but may be applied to any microscopic structure having a known relationship between its z-axis projection and x-y plane projection. This known relationship can represent allowable relationships between a height of the microscopic structure (along the z axis) and the area, length, radius or width of the microscopic structure on the x-y plane.

There is provided a method that may take advantage of the geometric shape of a bump to apply optical interferometric methods (for example, the dual wavelength digital holography) to extend the height range beyond prior the mentioned above limitations.

For simplicity of explanation the following methods are described in relation to phase information and amplitude information obtained by a DHM system but the mentioned below methods are applicable any interferometric system or method where phase detection and calculation algorithms are being used.

First Embodiment

Figure 5A:
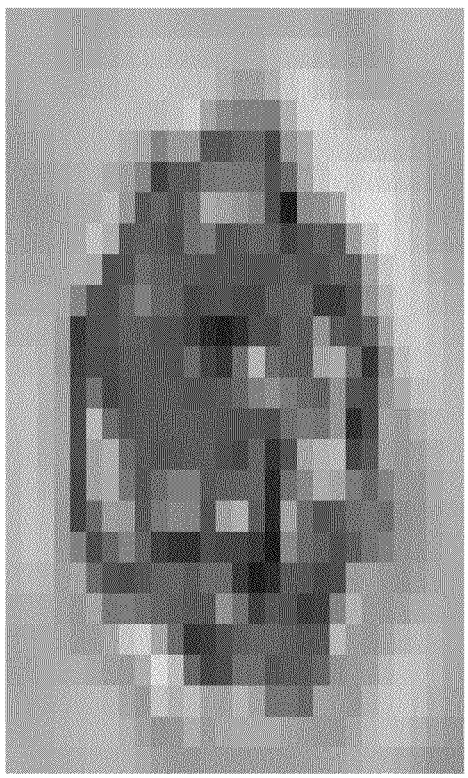
FIGS. 5a and 5b illustrate different phase information obtained of the same solder bump due to random noise.
Figure 5B:
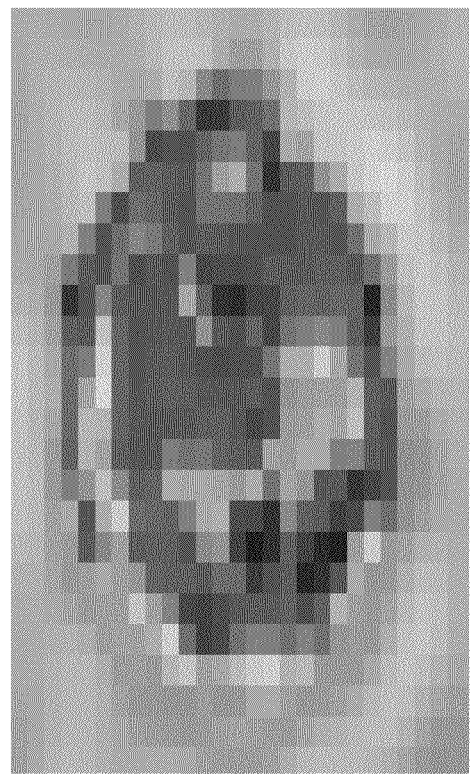
Figure 6:
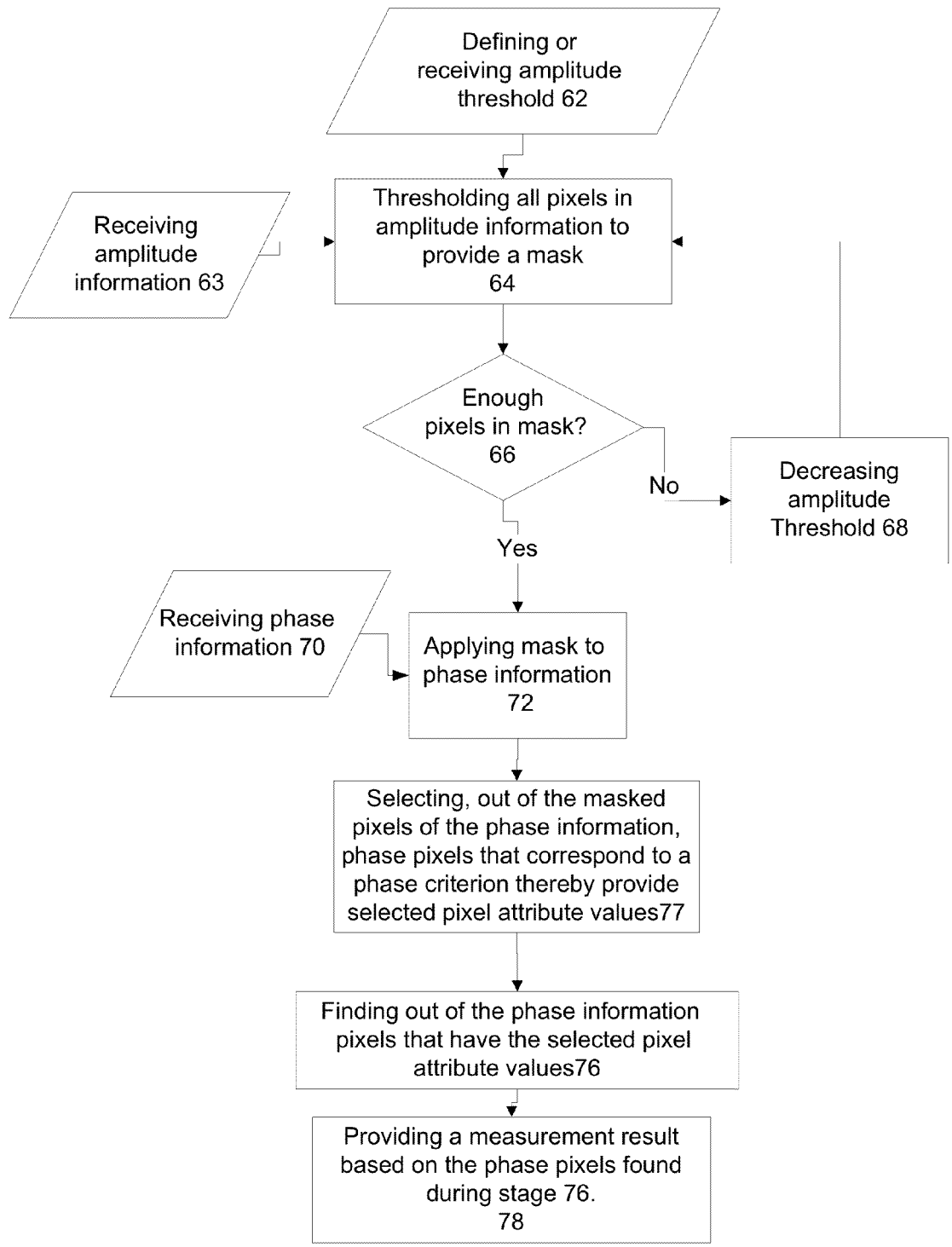
FIG. 6 illustrates a method according to an embodiment of the invention.

Phase noise is illustrated by FIGS. 5a and 5b that include different phase information (phase images 52 and 54) for the same bump—as they were taken at different points of time but while applying the same illumination and collection conditions.

Phase information can be processed to extract pixels that may be noisier then other pixels—or at least are expected to include too much noise.

A method is provided and may include singling out the significant pixel (or pixels) out of phase information pixels.

The entire bump phase information can be processed to choose phase information pixels that share the same attribute values such as have similar statistical qualities as the significant pixels.

The height of the bump can be determined based upon these found out pixels.

The method may start by defining or receiving (62) an amplitude threshold. The amplitude threshold can be either set by user or automatically learned from frame The selection process may be applied for each bump individually and may include stages 63-68.

Receiving amplitude information (63).

Using (64) an amplitude threshold to create a mask. The pixels of the mask are those that have an amplitude value above the amplitude threshold.

Checking (66) if the number of mask pixels (those included in the mask) is lower that a desirable value—if not enough mask pixels then adjusting (68) the amplitude threshold and going to step 64.

Receiving phase information (70) that is related to the same bump as the amplitude information.

Applying (72) the mask to the phase information—finding masked pixels of the phase information that correspond to the pixels of the mask.

Selecting (74), out of the masked pixels of the phase information, selected phase pixels that correspond to a phase criterion. 74 and finding the values of attributes of these pixels (selected pixels attribute values). An attribute can include the phase value of the selected phase pixels or a range or phase values. This can include singling out a pixel (or a group of pixels) that meets some specific statistical criteria (the criteria can be the maximal value, closest to average, median value, top x % etc.) that can be either learned, manually set or predefined.

Finding (76) out of the phase information phase pixels that have the selected pixel attribute values. This may include testing the entire phase information of the bump and creating a new mask based on pixels that share similar statistical qualities as the pixel(s) found on step 72.

Providing (78) a measurement result based on the phase pixels found during stage 76. This may include ignoring other phase information pixels and applying one or more processing operations on the found out phase information pixels. The processing may include calculating the average of all selected pixels or any other method that proves to yield valid results.

Stage 78 may include generating an approximation of the shape and size of the microscopic structure based on a predefined approximation of the shape of the microscopic structure and on the elected phase pixels. If, for example, the object is a bump then the predefined approximation is a half dome.

Figure 7:
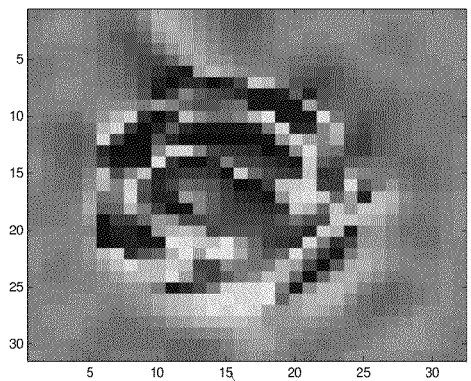
FIG. 7 illustrates various images received and generated during the execution of the method of FIG. 6 according to an embodiment of the invention.
Figure 7:
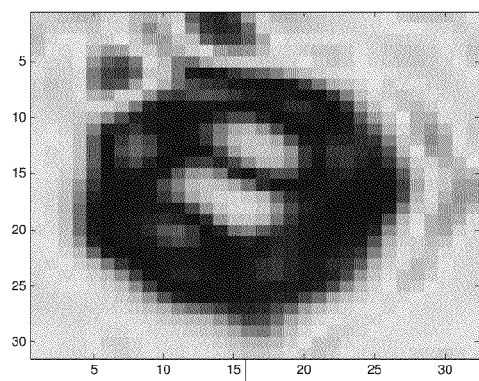
Figure 7:
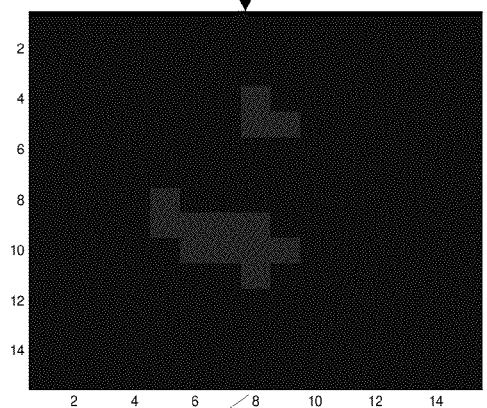
Figure 7:
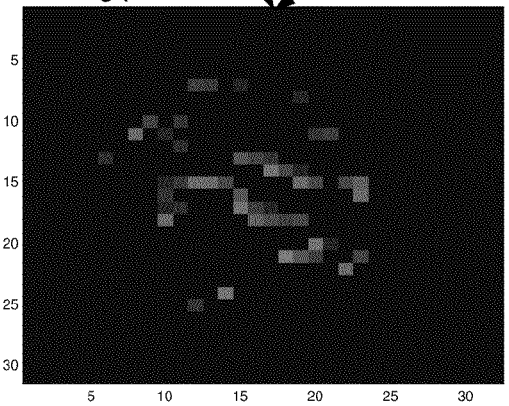

FIG. 7 illustrates various images that are generated during method 60 according to an embodiment of the invention.

These images include phase image 81, amplitude image 82 mask 83 and elected phase pixels 84. It is noted that an image is an example of information and that phase and amplitude information can be represented by information types that differ from images.

Figure 8:
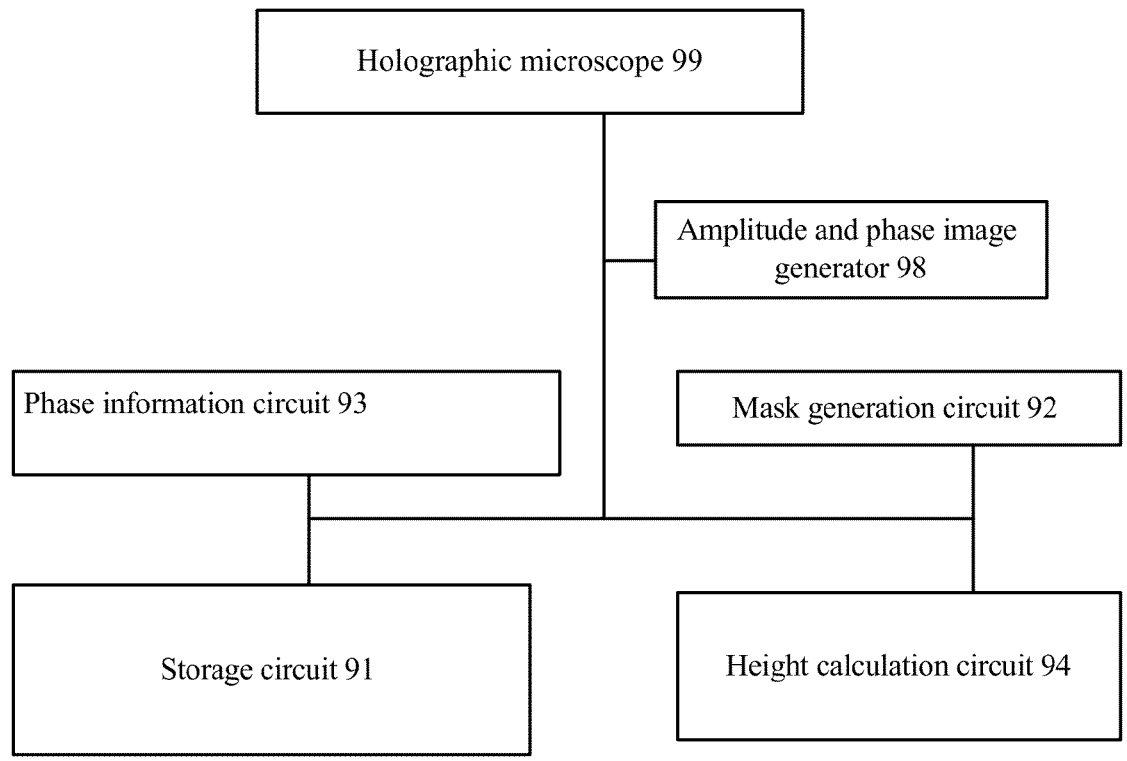
FIG. 8 illustrates a system according to an embodiment of the invention.

FIG. 8 illustrates a device 90 according to an embodiment of the invention.

The device 90 may include: (a) a storage circuit (91) arranged to store information that comprises amplitude information and phase information, wherein the information is indicative of a shape and a size of the microscopic structure; a mask generation circuit (92) arranged to threshold pixels of the amplitude information to provide a mask that comprises masked amplitude pixels; a phase information circuit (93) arranged to apply the mask on the phase information to provide masked phase pixels; select, out of the masked phase pixels, selected phase pixels that correspond to a phase criterion, the selected phase pixels have selected phase pixels attribute values; find, out of the phase information, elected phase pixels that have the selected phase pixel attribute values; a height calculation circuit (94) arranged to generate a height measurement result based the elected phase pixels, and an amplitude and phase image generator (98) arranged to convert an image obtained from a holographic microscope to a phase image and an amplitude image. FIG. 8 also illustrates a holographic microscope 99.

The mask generation circuit 92 may be arranged to check whether the mask has at least a predetermined number of pixels; wherein if the mask does not have the at least predetermined number of pixels then the mask generation circuit 92 may be arranged to lower the amplitude information to provide a modified amplitude threshold; and the phase information circuit 93 may be arranged to threshold the pixels of the amplitude information using the modified amplitude threshold.

The microscopic structure can be a bump such as a solder bump.

The phase criterion may represent a statistical criterion selected out of an average, a standard deviation, a weight average or a median.

The height calculation circuit 94 may be arranged to generate a height measurement result based on a predefined approximation of the shape of the microscopic structure and on the elected phase pixels.

Second Embodiment

For any semiconductor process there is an expected (nominal) bump height ($H_0$) as well as expected tolerances that the bump height. These tolerances can be represented by minimal and maximal tolerable heights ($H_{min}$, and $H_{max}$). Also, there is an expected relationship (diameter to height ratio) between the diameter of a bump and the height of the bump.

It is noted that a combination of the second and first embodiments can be provided. For example, method 30 can be executed on pixels that are selected by method 60. Yet for another example, the devices of FIGS. 4 and 8 can be combined.

Figure 1:
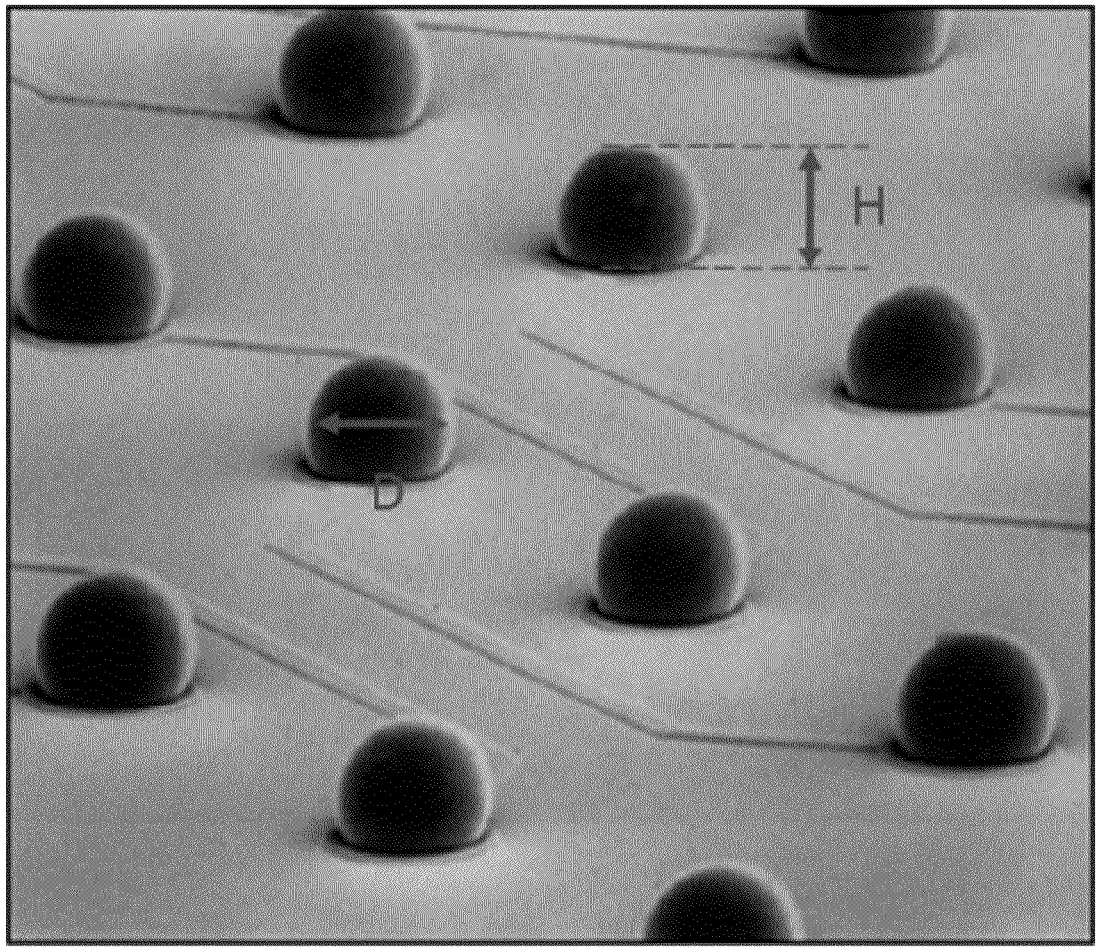
FIG. 1 illustrates a prior art portion of a semiconductor chip with multiple solder bumps.
Figure 2A:
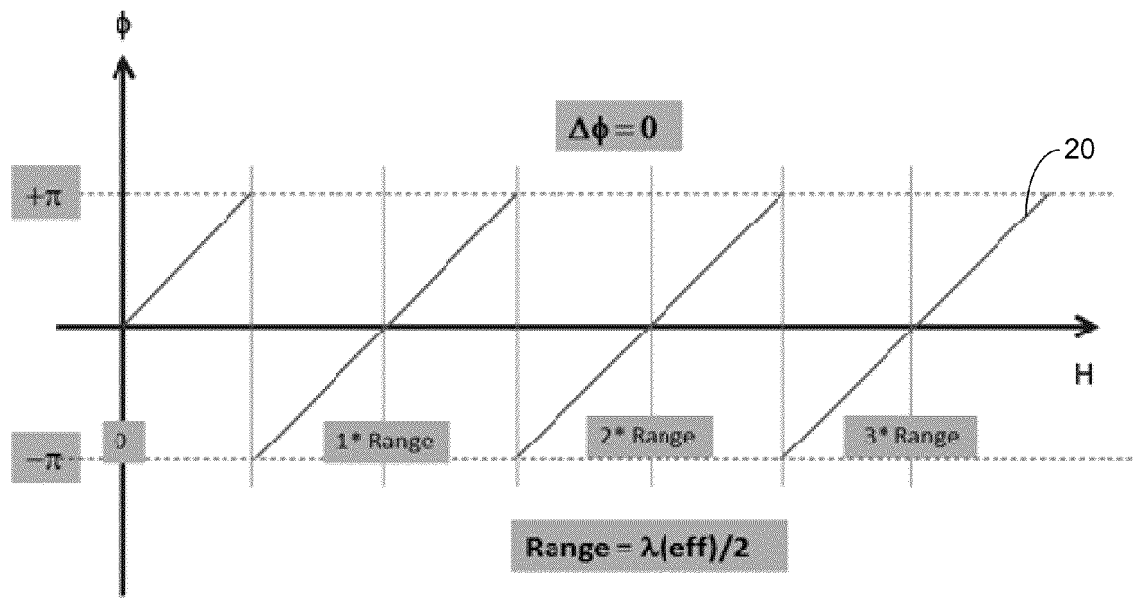
FIGS. 2a and 2b illustrate phase height ambiguities for two different phase offsets.
Figure 2B:
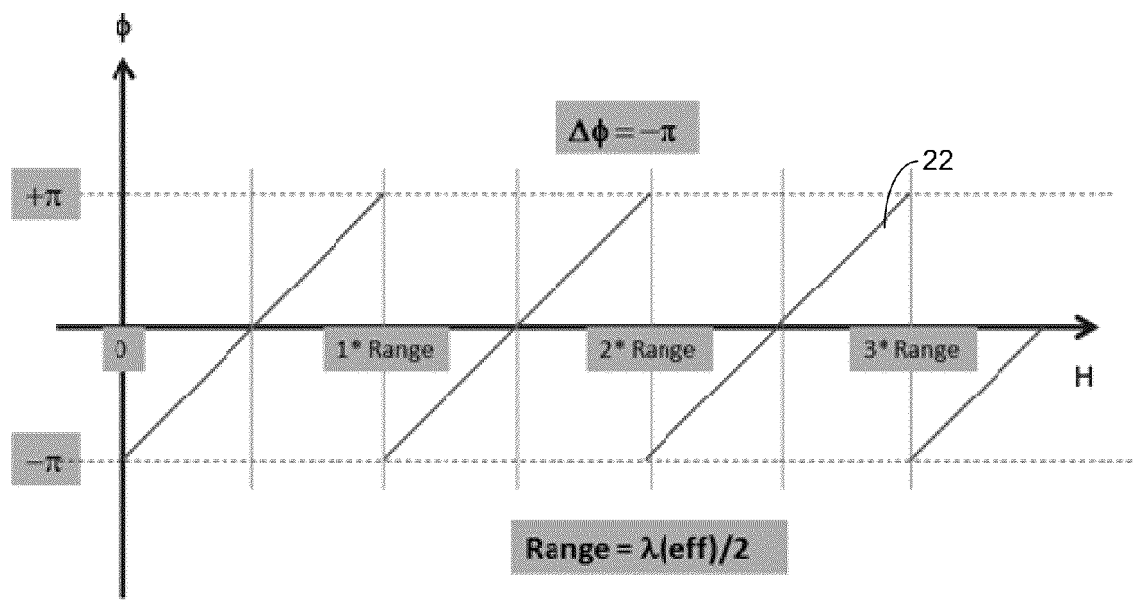
Figure 3:
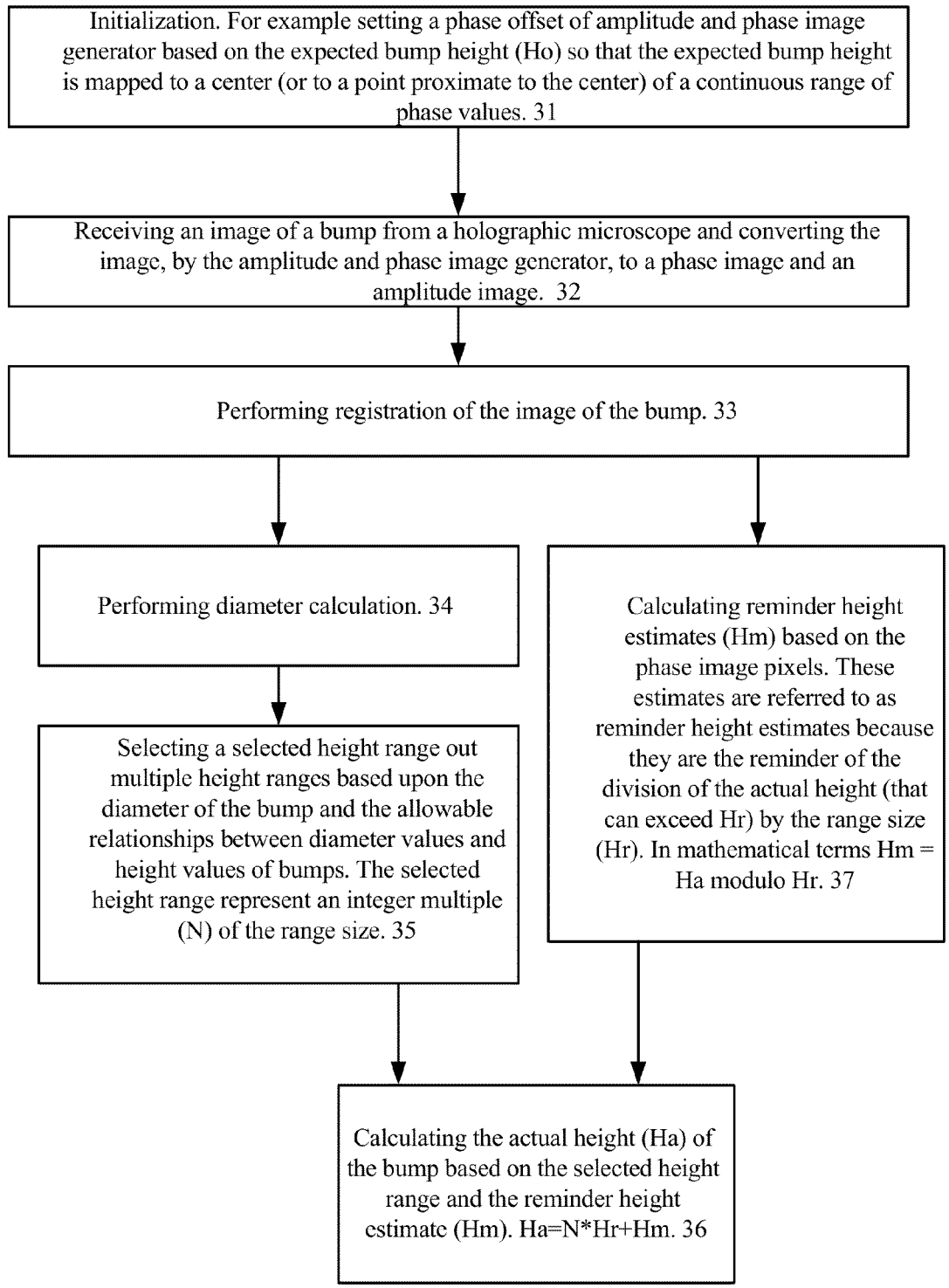
FIG. 3 illustrates a method according to an embodiment of the invention.

FIG. 3 illustrates a method 30 for determining a height of a bump according to an embodiment of the invention.

Method 30 starts by initialization stage 31. The initialization stage may include receiving an expected height of the bump, and receiving expected relationships between diameter values and height values of bumps. This information is usually provided by the manufacturer of the bump.

Stage 31 may include setting a phase offset of a amplitude and phase image generator based on the expected bump height (Ho) so that the expected bump height is mapped to a center (or to a point proximate to the center) of a continuous range of phase value. This may reduce the number of height measurements that are mapped to discontinuities of the relationship between phase information and height.

For example, if the expected height is about the range size ($H_0 \sim Hr$), then the desired phase offset should be set to zero. If the expected height is about half of the range size ($H_0 \sim 0.5*Hr$), the desired phase offset should equal minus pi.

Stage 31 may be followed by stage 32 of receiving an image of a bump from a holographic microscope and converting the image, by the amplitude and phase image generator, to a phase image and an amplitude image.

Stage 32 may be followed by stage 33 of performing registration of the image of the bump. This stage may include finding the coordinates of the bump that its image is being processed and correlating this image with a known bump. For example, if an array of bumps is being inspected than the measurements of the bump that is located at the i'th row and the j'th column of the array (BUMP(i,j)) should be matches to the image of that bump. This matching is referred to as registration.

Stage 33 may be followed by stages 37 and 34.

Stage 37 may include calculating reminder height estimates (Hm) based on the phase image pixels. These estimates are referred to as reminder height estimates because they are the reminder of the division of the actual height (that can exceed Hr) by the range size (Hr). In mathematical terms Hm=Ha modulo Hr.

Stage 33 may include calculating the reminder height estimates by a linear or non-linear mapping.

An example of a linear mapping includes Hm=k*PHASE while k is a calibration parameter calculate in the process of tool integration (using well defined height standard).

Stage 34 may include performing diameter calculation. This may include detecting a bump edge and fitting the bump edge to circle thereby allowing diameter calculations. This stage may be applied on the amplitude image.

Stage 34 may be followed by stage 35 of selecting a selected height range out multiple height ranges based upon the diameter of the bump and the allowable relationships between diameter values and height values of bumps. The selected height range represent an integer multiple (N) of the range size.

For each semiconductor device, there is well known and expected bump diameter to height ratio range. On the second hand, the range size (Hr) is well defined by effective wave length. Therefore, an explicit empirical mapping between N (N is the "modulo" multiplier) and diameter can be created. For example, for bumps with $H_0 \sim \frac{3}{4}D$, the following LUT is valid:

If $H_0 < D < 2H_0$ then N=1.
If $D < H_0$ then N=0.
If $D > 2H_0$ then N=2.

Stages 34 and 35 are followed by stage 36 of calculating the actual height (Ha) of the bump based on the selected height range and the reminder height estimate (Hm). Ha=N*Hr+Hm.

Stage 36 may include calculating the actual height of each phase image pixel (or of some of these pixels) and processing the actual height values of these pixels.

Stage 36 can include applying a phase un-warping algorithm based on diameter of the bump the pre-defined mapping that assists in selecting the selected height range.

For example, assuming given the mentioned above mapping and the phase offset defined in stage 32:
If pixel on bump has height=Hm, and diameter of that bump is D=0.8H$_0$, that means, Ha=Hm (midget bump).
If pixel on bump has height=Hm, and diameter of that bump is D=1.3H$_0$, that means, Ha=1*Hr+Hm (normal bump)
If pixel on bump has height=Hm, and diameter of that bump is D=2.5H$_0$, that means, Ha=2*Hr+Hm (giant bump).

For this kind of N definition, the method that can provide phase readings for Hr is capable to measure solder bumps height between 0 to 3*Hr height. The actual range resulting of the proposed method may be limited by optical interferometric focus depth and empiric ability of mapping between diameter and height.

Figure 4:
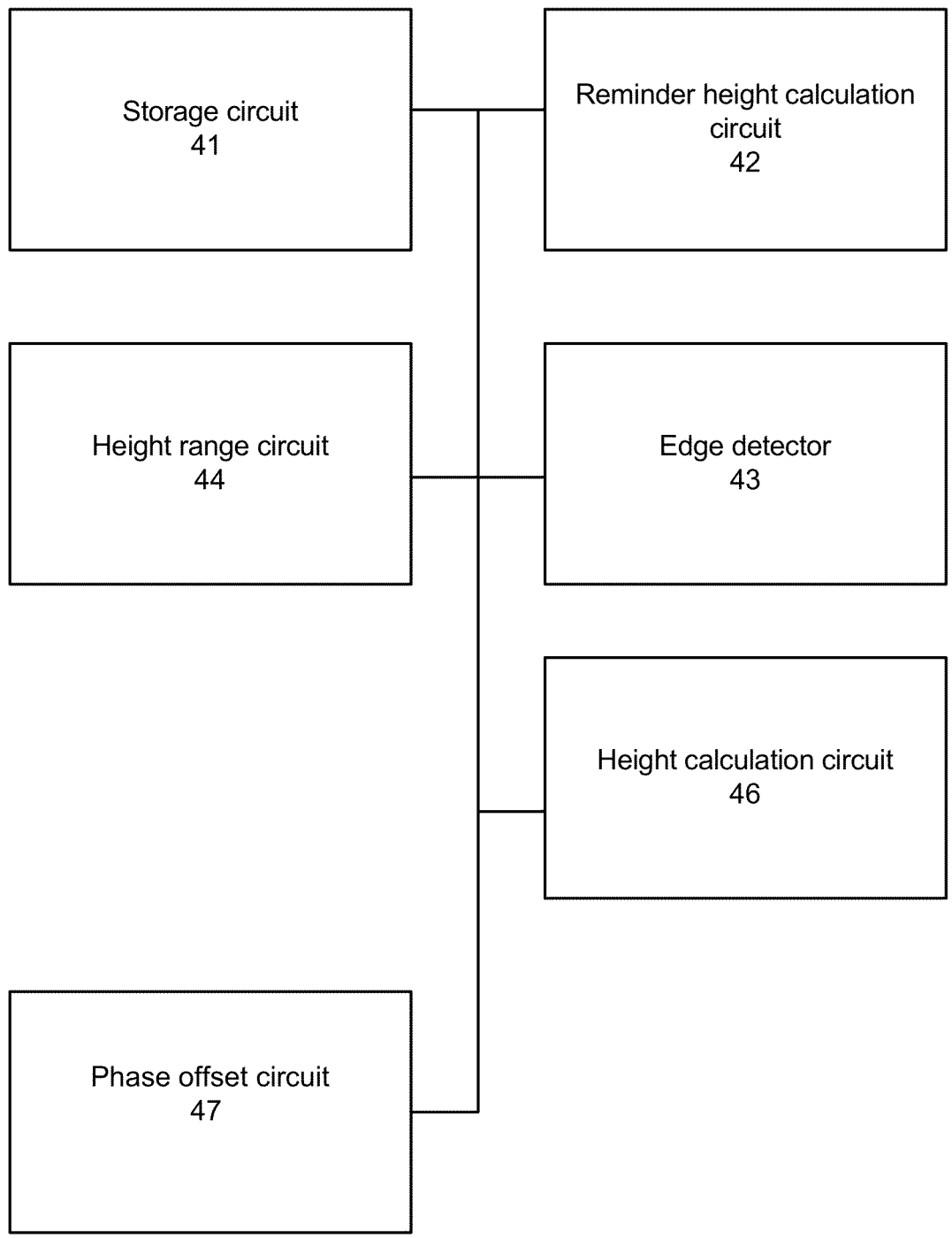
FIG. 4 illustrates a system according to another embodiment of the invention.

FIG. 4 illustrates a device 40 according to an embodiment of the invention.

Device 40 may include: (a) a storage circuit 41 for storing a phase image and an amplitude image of the microscopic structure; (b) a reminder height calculation circuit 42 arranged to calculate reminder height estimates based on the phase image pixels; (c) an feature extractor 43 arranged to detect the edge of the microscopic structure on a surface of an object; (d) a height range circuit 44 arranged to calculate a size attribute of the microscopic structure based on a size of a shape defined by the edge of the microscopic structure and to select a selected height range out multiple height ranges based upon the size attribute of the microscopic structure and an allowable relationship between the size attribute and height values of the microscopic structure; and (e) a height calculation circuit (46) arranged to calculate an actual height of the microscopic structure based on the selected height range and the reminder height estimate.

Each of the mentioned circuits may include hardware components.

The device 40 may include a phase offset circuit 47 that may be arranged to set a phase offset of an interferometer 49 that may be arranged to obtain the phase image and the amplitude image in response to an expected height of the microscopic structure.

The microscopic structure may be a bump and wherein the size attribute is a diameter of the bump.

The height calculation circuit 46 may be arranged to calculate actual height values form multiple phase image pixels of the phase image; and process the actual height values of the multiple phase image pixels to provide the actual height of the microscopic structure.

The phase offset circuit 47 may be arranged to set a phase offset of the interferometer so that the expected bump height is mapped to a center of a continuous range of phase values.

Any of the methods above can be executed by a computer that executed instructions stored in a non-transitory computer readable medium. The devices can be a part of a metrology tool, can be stand alone devices, can obtain the phase and amplitude information or receive such information.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A device for measuring a height of a microscopic structure, the device comprises: a storage circuit arranged to store information that comprises amplitude information and phase information, wherein the stored information is indicative of a shape and a size of the microscopic structure; a mask generation circuit arranged to threshold pixels of the amplitude information to provide a mask that comprises masked amplitude pixels that have amplitude values above an amplitude threshold; a phase information circuit arranged to apply the mask on the phase information to provide masked phase pixels; select, out of the masked phase pixels, selected phase pixels that form a part of the masked phase pixels and correspond to a phase criterion, the selected phase pixels have selected phase pixels attribute values; find, out of the phase information, elected phase pixels that have the selected phase pixel attribute values; and a height calculation circuit arranged to generate a height measurement result based the elected phase pixels.

2. The device according to claim 1, wherein the mask generation circuit is arranged to check whether the mask has at least a predetermined number of pixels; wherein if the mask does not have the at least predetermined number of pixels then the mask generation circuit is arranged to lower the amplitude information to provide a modified amplitude threshold; and wherein the phase information circuit is arranged to threshold the pixels of the amplitude information using the modified amplitude threshold.

3. The device according to claim 1, wherein the microscopic structure is a solder bump.

4. The device according to claim 3, wherein the mask generation circuit is arranged to check whether the mask has at least a predetermined number of pixels; wherein if the mask does not have the at least predetermined number of pixels then:
  (a) the mask generation circuit is arranged to lower the amplitude information to provide a modified amplitude threshold and
  (b) the phase information circuit is arranged to threshold the pixels of the amplitude information using the modified amplitude threshold.

5. The device according to claim 3, wherein the phase criterion represent a statistical criterion selected out of an average, a standard deviation, a weight average or a median.

6. The device according to claim 3, wherein the height calculation circuit is arranged to generate a height measurement result based on a predefined approximation of the shape of the microscopic structure and on the elected phase pixels.

7. The device according to claim 1, wherein the phase criterion represent a statistical criterion selected out of an average, a standard deviation, a weight average or a median.

8. The device according to claim 1, wherein the height calculation circuit is arranged to generate the height measurement result based on a predefined approximation of the shape of the microscopic structure and on the elected phase pixels.

9. A method for measuring a height of a microscopic structure, the method comprises: receiving or generating information that comprises amplitude information and phase information, wherein the stored information is indicative of a shape and a size of the microscopic structure; thresholding pixels of the amplitude information to provide a mask that comprises masked amplitude pixels that have amplitude values above an amplitude threshold; applying the mask on the phase information to provide masked phase pixels; selecting, out of the masked phase pixels, selected phase pixels that form a part of the masked phase pixels and correspond to a phase criterion, the selected phase pixels have selected phase pixels attribute values; finding, out of the phase information, elected phase pixels that have the selected phase pixel attribute values; and generating a height measurement result based the elected phase pixels.

10. The method according to claim 9, comprising: checking whether the mask has at least a predetermined number of pixels; wherein if the mask does not have the at least predetermined number of pixels then lowering the amplitude information to provide a modified amplitude threshold; and thresholding the pixels of the amplitude information using the modified amplitude threshold.

11. The method according to claim 9, wherein the microscopic structure is a solder bump.

12. The method according to claim 11, comprising: checking whether the mask has at least a predetermined number of pixels; wherein if the mask does not have the at least predetermined number of pixels then:
  (a) lowering the amplitude information to provide a modified amplitude threshold and
  (b) thresholding the pixels of the amplitude information using the modified amplitude threshold.

13. The method according to claim 11, wherein the phase criterion represent a statistical criterion selected out of an average, a standard deviation, a weight average, a median.

14. The method according to claim 11, comprising generating a height measurement result by generating an approximation of the shape and size of the microscopic structure based on a predefined approximation of the shape of the microscopic structure and on the elected phase pixels.

15. The method according to claim 9, wherein the phase criterion represent a statistical criterion selected out of an average, a standard deviation, a weight average, a median.

16. The method according to claim 9, comprising generating the height measurement result by generating an approximation of the shape and size of the microscopic structure based on a predefined approximation of the shape of the microscopic structure and on the elected phase pixels.

* * * * *